United States Patent
Lentz et al.

(10) Patent No.: US 7,044,961 B2
(45) Date of Patent: May 16, 2006

(54) EPTFE GRAFT-STENT COMPOSITE DEVICE

(75) Inventors: David J. Lentz, Randolph, NJ (US); Edward Dormier, Rockaway, NJ (US)

(73) Assignee: Meadox Medicals, Inc., Oakland, NJ (US)

( * ) Notice: Subject to any disclaimer, the term of this patent is extended or adjusted under 35 U.S.C. 154(b) by 89 days.

(21) Appl. No.: 09/957,964

(22) Filed: Sep. 21, 2001

(65) Prior Publication Data
US 2002/0040237 A1    Apr. 4, 2002

Related U.S. Application Data

(60) Continuation of application No. 09/324,303, filed on Jun. 2, 1999, now Pat. No. 6,309,343, which is a division of application No. 08/784,842, filed on Jan. 17, 1997, now Pat. No. 5,961,545.

(51) Int. Cl.
*A61F 2/82* (2006.01)

(52) U.S. Cl. ..................... 623/1.13; 623/1.17

(58) Field of Classification Search ............... 623/1.13, 623/1.17, 901, 909, 1.44, 1.49, 1.54, 23.7; 606/191, 194, 198; 600/36
See application file for complete search history.

(56) References Cited

U.S. PATENT DOCUMENTS

| | | | |
|---|---|---|---|
| 3,657,744 A | 4/1972 | Ersek | |
| 4,300,244 A | 11/1981 | Bokros | |
| 4,409,172 A | 10/1983 | Ward, Jr. et al. | |
| 4,732,152 A | 3/1988 | Wallsten et al. | |
| 4,969,458 A | 11/1990 | Wiktor | |
| 5,078,726 A | 1/1992 | Kreamer | |
| 5,123,917 A | 6/1992 | Lee | |
| 5,282,824 A | 2/1994 | Gianturco | |
| 5,330,500 A | 7/1994 | Song | |
| 5,366,504 A | 11/1994 | Anderson et al. | |
| 5,383,926 A | 1/1995 | Lock et al. | |
| 5,387,235 A | 2/1995 | Chuter | |
| 5,389,106 A | 2/1995 | Tower | |
| 5,441,515 A * | 8/1995 | Khosravi et al. | ........... 606/194 |
| 5,443,500 A * | 8/1995 | Sigwart | .................... 623/1.17 |
| 5,456,713 A | 10/1995 | Chuter | |
| 5,507,769 A | 4/1996 | Marin | |
| 5,507,771 A | 4/1996 | Gianturco | |
| 5,522,881 A | 6/1996 | Lentz | |

(Continued)

FOREIGN PATENT DOCUMENTS

DE      3902364      8/1989

(Continued)

OTHER PUBLICATIONS

Lawrence, Jr. D.D., Charnsangavej, C., Wright, K.C., Gianturco, C., and Wallace, S., Percutaneous Endovascular Graft: Experimental Evaluation. Radiology 1986; 163:357-360.

*Primary Examiner*—Paul B. Prebilic
(74) *Attorney, Agent, or Firm*—Hoffmann & Baron, LLP

(57) ABSTRACT

An implantable intraluminal device includes a multilayer composite tubular device supporting one or more stents between the layer thereof. A first porous elongate tube includes an exterior surface and an interior luminal surface. A radially expandable member is disposed about the exterior surface of the first tube. A second porous elongate tube is disposed concentrically over the first tube and is secured thereto so that the radially expandable member is longitudinally immobilized therebetween.

4 Claims, 4 Drawing Sheets

U.S. PATENT DOCUMENTS

| | | | |
|---|---|---|---|
| 5,562,726 A | 10/1996 | Chuter | |
| 5,618,299 A | 4/1997 | Khosravi et al. | |
| 5,665,117 A | 9/1997 | Rhodes | |
| 5,723,004 A * | 3/1998 | Dereume et al. | 623/1.35 |
| 5,735,892 A | 4/1998 | Myers et al. | |
| 5,788,626 A * | 8/1998 | Thompson | 623/1.15 |
| 5,797,951 A | 8/1998 | Mueller | |
| 5,824,038 A | 10/1998 | Wall | |
| 5,824,054 A | 10/1998 | Khosravi et al. | |
| 5,843,166 A * | 12/1998 | Lentz et al. | 623/1.13 |
| 5,961,545 A * | 10/1999 | Lentz et al. | 623/1.39 |
| 6,010,529 A | 1/2000 | Herweck et al. | |
| 6,287,315 B1 * | 9/2001 | Wijeratne et al. | 606/108 |
| 6,398,803 B1 * | 6/2002 | Layne et al. | 623/1.13 |

FOREIGN PATENT DOCUMENTS

| | | |
|---|---|---|
| EP | 0 657 147 | 6/1995 |
| EP | 0 689 805 | 1/1996 |
| EP | 0 737 453 | 10/1996 |
| SU | 1457921 A1 | 2/1989 |
| WO | WO 95/02377 | 1/1995 |
| WO | WO 95/05132 | 2/1995 |
| WO | WO 95/29647 | 11/1995 |
| WO | WO 96/00103 | 1/1996 |
| WO | WO 96/10967 | 4/1996 |
| WO | WO 96/22745 | 8/1996 |
| WO | WO 96/28115 | 9/1996 |
| WO | WO 96/33672 | 10/1996 |
| WO | WO 96/35577 | 11/1996 |

* cited by examiner

EPTFE GRAFT-STENT COMPOSITE DEVICE

This application is a continuation of U.S. application Ser. No. 09/324,303, filed on Jun. 2, 1999, now U.S. Pat. No. 6,309,343 B1 which issued on Oct. 30, 2001, which is a divisional of U.S. application Ser. No. 08/784,842, filed on Jan. 17, 1997, now U.S. Pat. No. 5,961,545 which issued on Oct. 5, 1999.

FIELD OF INVENTION

The present invention relates generally to tubular implantable prosthetic devices such as vascular grafts and other endoprostheses. More particularly, the present invention relates to a graft formed of porous expanded polytetrafluoroethylene (ePTFE) which supports a stent in an ePTFE composite graft-stent device.

BACKGROUND OF THE INVENTION

Intraluminal devices such as grafts and stents are known for treating stenosis, stricture, aneurysms and the like. These devices may be implanted either transluminally in a minimally invasive procedure or may be surgically implanted.

Such intraluminal devices provide a technique for expanding a constricted vessel or for maintaining an open passageway through a vessel. One common technique used to hold open a blocked or constricted vessel such as a blood vessel is to employ a vascular stent. Stents are implantable intraluminal devices typically formed of wire which may be radially expanded to hold open constricted vessels. Thus, wire stents are useful to prevent restenosis of a dilated vessel or to eliminate the danger of reocclusion of the vessel. In addition, wire stents can also be used to reinforce various lumen in danger of collapse. However, stents are not generally designed as conduits or bypass devices.

Intraluminal or endoprosthetic grafts, however, are designed as bypass devices which allow fluid flow therethrough. Often, these devices are percutaneously implanted within the vascular system to reinforce collapsing, partially occluded, weakened or abnormally dilated localized sections of, e.g., a blood vessel. Grafts may also be surgically implanted by anastomosis to replace a badly damaged portion of vessel.

Vascular grafts may be manufactured from a variety of bio-compatible materials. For example, it is well known to use extruded tubes of polytetrafluoroethylene (PTFE) as vascular grafts. PTFE is particularly suitable as it exhibits superior biocompatibility. PTFE tubes may be used as vascular grafts in the replacement or repair of blood vessels because PTFE exhibits low thrombogenicity. Further, expanded PTFE (ePTFE) tubes have a microporous structure which allows natural tissue ingrowth and cell endothelialization once implanted into the vascular system. This contributes to long term healing and graft patency.

Grafts formed of ePTFE have a fibrous state which is defined by interspaced nodes interconnected by elongated fibrils. The spaces between the node surfaces that are spanned by the fibrils are defined as the internodal distance (IND). The art is replete with examples of vascular grafts made of microporous ePTFE tubes useful as vascular grafts. The porosity of an ePTFE vascular graft is controlled by varying the IND of the microporous structure of the tube. An increase in the IND within a given structure results in enhanced tissue ingrowth, as well as, cell endothelialization along the inner surface thereof. Increasing the porosity of the tubular structure, however, reduces the ability of the graft to retain a suture placed therein during implantation and tends to exhibit low axial tear strength. In order to strike an effective balance between porosity and radial strength, multi-layer ePTFE tubes have been developed. The porosity of these multilayered tubes vary as between the outer and inner layers to achieve a composite structure having sufficient porosity for tissue ingrowth and cell endothelialization while still retaining sufficient radial strength.

It is known in the art to use stents in combination with vascular grafts and other endoprostheses. Stents may be positioned at one or both ends of a graft to support the graft within a portion of the vessel. Thus positioned, the stents help fix the graft to the vessel wall. In addition, stents serve to keep the lumen open and to anchor the graft in place. A single stent may also be employed in combination with a graft to allow the graft to "float" downstream toward the affected vessel. Once properly positioned, the single stent is expanded to anchor the graft in place.

Several techniques for securing one or more stents to a graft are known. For example, hooks or barbs extending from the stent have been used for securing stents to a graft. Alternatively, a stent may be sutured to a graft. Each of these techniques requires either specialized stent attachment means or secondary procedures to secure the stents to the graft.

Traditional stents have various shapes and sizes depending upon their intended function. For example, structures which have previously been used as stents include coiled stainless steel springs, helically wound coiled springs manufactured from an expandable heat-sensitive material, expanding stainless steel stents formed of stainless steel wire in a "zig-zag" pattern, cage-like devices made from malleable metal, and flexible tubes having a plurality of separate expandable ring-like scaffold members which permit radial expansion of a graft. Each of these devices is designed to be radially compressible and expandable so that it will easily pass through a blood vessel in a collapsed state and can be radially expanded to an implantable size after the target area of the vessel has been reached. Radial expansion and contraction of each of these causes associated longitudinal expansion and contraction of the stent.

Such expandable stents may be supported between the layers of a multi-layer tubular graft. The expandable stent would anchor and support the multi-layer tube within the lumen. Upon radial expansion, the stent would hold the graft outwardly against the inner wall of the lumen.

One example of such a graft-stent combination is shown in U.S. Pat. No. 5,123,917 issued to Lee et al. A stent-graft combination shown therein includes a plurality of separate scaffold members (stents) mounted between an inner tube and an outer tube forming the multi-layer graft. In one embodiment of this invention, the scaffold members are free floating within an intermediate pocket formed by the inner and outer tubes. In another embodiment, the scaffold members are adhesively affixed to the outer surface of the inner tube. In yet another embodiment of this invention, the inner and outer tubes are adhered to each other in such a manner that separate pockets are formed in which individual scaffold members are placed within each pocket.

In each of these different embodiments of the '917 patent, radial expansion of the scaffold member causes a change in the longitudinal expanse thereof. Thus, a drawback to the device shown in the '917 patent is that the net length of the scaffold member increases as the graft contracts. Accordingly, this increase in the net length of the scaffold member increases the stress forces on the graft as well as tends to delaminate the layers. Thus, these stress forces increase the likelihood that the inner tube will become separated from the outer tube and/or that the graft will tear upon expansion of the scaffold members.

Accordingly, it would be desirable to provide an improved intraluminal device, in particular, an ePTFE graft-stent composite device with improved radial strength that allows for the deployment of a stent and graft simultaneously with the stent already permanently positioned on the graft such that additional stress is not placed on the graft by the stent upon expansion.

SUMMARY OF THE INVENTION

In accordance with the present invention, an improved composite graft-stent device is provided. More particularly, the present invention is formed from two non thrombogenic tubes which are laminated or fused together with one or more stents secured therebetween. This composite device is then expanded to place it in intimate contact with the inner surface of the lumen in which it is positioned.

The composite device is preferably an implantable intraluminal device with a first porous tube that has two opposed ends, an interior luminal surface and an exterior surface. The composite device also contains a second porous tube which is disposed concentrically about the exterior surface of the first tube and is secured to the exterior surface of the first tube. A radially expandable member is disposed about the exterior surface of the first tube and is longitudinally immobilized between the first and second tubes when they are secured. In the present invention, the second tube is secured to the first tube by fusion or by lamination.

The radially expandable member between the two tubes includes a longitudinal expanse. As used herein, the term "longitudinal expanse" means the width of the radially expandable member as measured along the axis of the tube. In the present invention, when the member is expanded, there is no distortion along the longitudinal expanse of the member, e.g., the width remains constant as the member is expanded. The member is preferably an expandable stent.

The expandable stent of the invention includes an elongated element with a first end and a second opposed end. In one embodiment of the invention, the elongated element is formed in a generally circular configuration with the first end adjacent to and overlapping the second opposed end. The stent is expandable through the relative movement of the first end with respect to the second opposed end.

In another embodiment of the invention, the end extent of the first end of the elongated element has a plurality of second end engagement means for engaging the distal end of the second end to provide finite adjustability to the stent.

In yet another embodiment of the present invention, the radially expandable stent includes an elongate element having a first end and a second opposed end. This elongate element is formed in a generally circular configuration with the first and second ends in axial alignment to each other. In this embodiment of the invention, the second end has an elongate open-ended channel wherein radial expansion is achieved by movement of the first end out of the open-ended channel of the second end.

The implantable intraluminal device of the present invention is preferably fabricated out of a biocompatible metal. Most preferably, the implantable intraluminal device is stainless steel, platinum, gold, nitinol, tantalum and alloys thereof.

The first and second tubes of the present invention are preferably fabricated out of a biocompatible material. Most preferably, the first and second tubes are fabricated out of expanded polytetrafluoroethylene (ePTFE).

In the present invention, a stent may be disposed about the exterior surface of the first tube adjacent to either of the first or second ends. Alternatively, a stent may be disposed about the exterior surface of the first tube at both ends. In yet another embodiment, a plurality of stents may be disposed about the exterior surface of the fist tube and longitudinally spaced between stents located at the first and second ends of the device.

In the present invention, the device may be expanded by an inflation force. Preferably, the inflation force is supplied by inflating a balloon catheter.

The process of the present invention hereby incorporates by reference all of the limitations described above for the intraluminal implantable device. By way of summary, in the process of the invention an implantable intraluminal device is provided which includes a first luminal porous tube having first and second ends, an interior luminal surface and an exterior surface. One or more radially expandable members is/are then radially disposed about the exterior surface of the first tube. A second porous tube is then concentrically positioned over the first tube and the radially expandable member(s). The first tube is then secured to the second tube so that one or more expandable members is/are immobilized along the longitudinal axis of the first and second tubes.

BRIEF DESCRIPTION OF THE DRAWINGS

The present invention can be further understood with reference to the following description in conjunction with the appended drawings, wherein like elements are provided with the same reference numbers. In the drawings.

DETAILED DESCRIPTION OF THE PREFERRED EMBODIMENT

Figure 1:
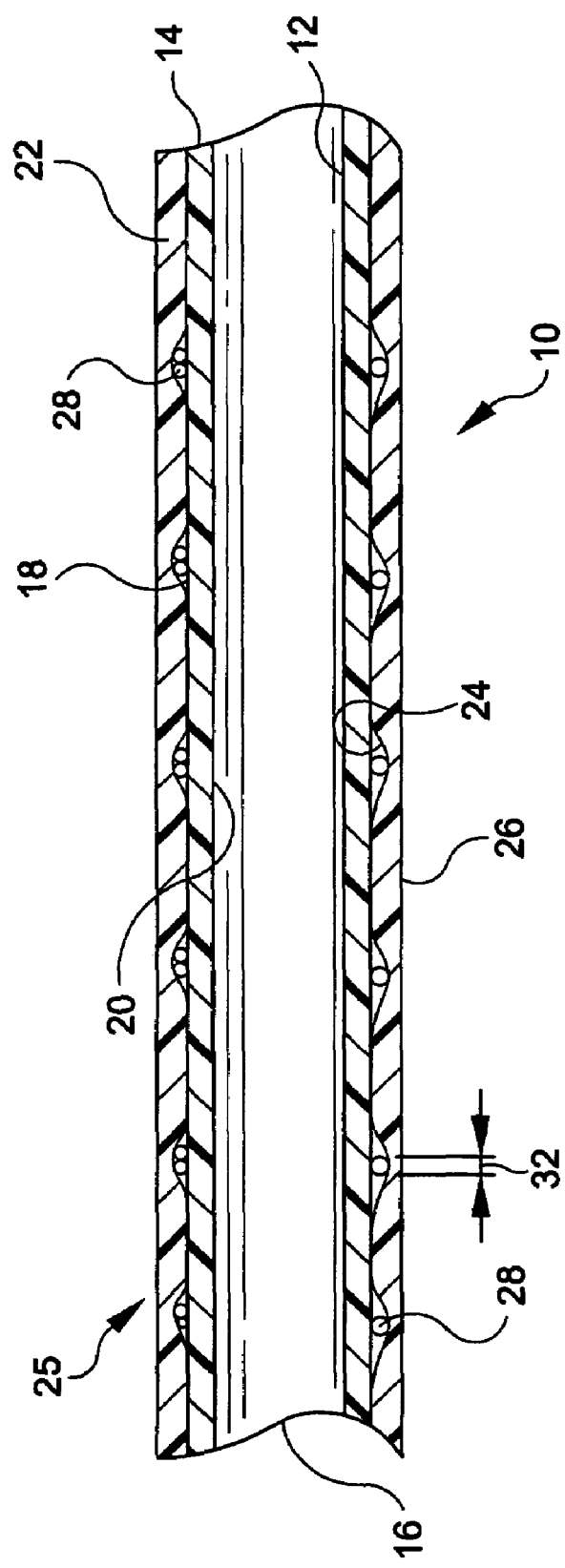
FIG. 1 is a longitudinal cross-section of the composite graft-stent of the present invention.

Now turning to FIG. 1, a longitudinal cross-section of the preferred embodiment of the graft-stent composite device 10 is shown. This device 10 includes a multilayer graft 25 which is formed of inner and outer tubes 12 and 22 that are preferably formed of expandable polytetrafluoroethylene (ePTFE). Although it is preferred that tubes 12 and 22 be made of ePTFE, any appropriate bio-compatible material, such as porous polyurethane, is also contemplated. Other potential materials for this application include DACRON, a proline mesh or the like. Ideally, the material should be inert and should not promote a significant amount of scar formation.

Graft 25 has first and second opposed ends 14 and 16, respectively. Tube 12 includes an exterior surface 18 and an interior luminal surface 20. Tube 22 has an interior surface 24 and an exterior vascular surface 26. Tube 22 is disposed concentrically over the exterior surface 18 of tube 12 to form the multilayer graft 25.

A plurality of longitudinally spaced stents 28 are disposed between the exterior surface 18 of tube 12 and the interior surface 24 of tube 22. As will be described hereinbelow, each stent 28 is of the type which may be radially expanded. Stents 28 are longitudinally immobilized between tubes 12 and 22 when they are secured to each other. The stents 28 are positioned at spaced locations along the multi-layer graft 25 in numbers which may be selected based on use and application of the device 10.

FIG. 1 shows tubes 12 and 22 laminated together to form graft 25 with stents 28 disposed therebetween. Although FIG. 1 shows tubes 12 and 22 laminated together, any appropriate method of securement, such as fusion, is contemplated. The lamination of tubes 12 and 22 causes stents 28 to be immobilized along the longitudinal axis of the multi-layer graft 25.

Figure 2:
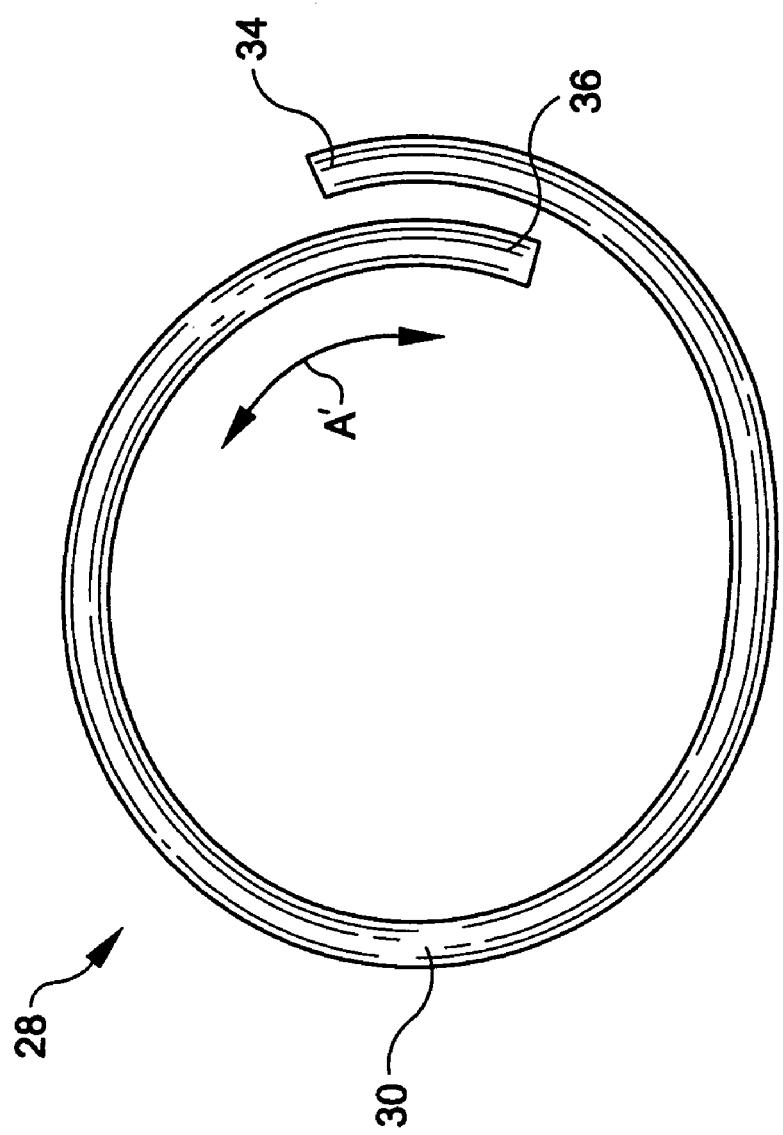
FIG. 2 is a front view of the "key-ring" type stent employed in the composite graft-stent of FIG. 1.

Now turning to FIG. 2, a preferred embodiment of stent 28 is shown. Stent 28 may be formed from a wire 30 which is wound in the shape of a simple circle generally described as a "key-ring." The circular wire 30 includes a first end 34 adjacent to and overlapping a second opposed end 36. The wire 30 is radially expandable by movement of first end 34 and second end 36 in opposing directions relative to each other as indicated by arrow A. Radial expansion is accomplished by, for example, the expansion of a balloon catheter exerting radial pressure on wire 30. This radial expansion is achieved without a change in the longitudinal expanse 32 of the wire 30 which is shown in FIG. 1. While balloon expansion is described, it is also contemplated that stent 28 may be of the self-expanding variety.

Figure 3:
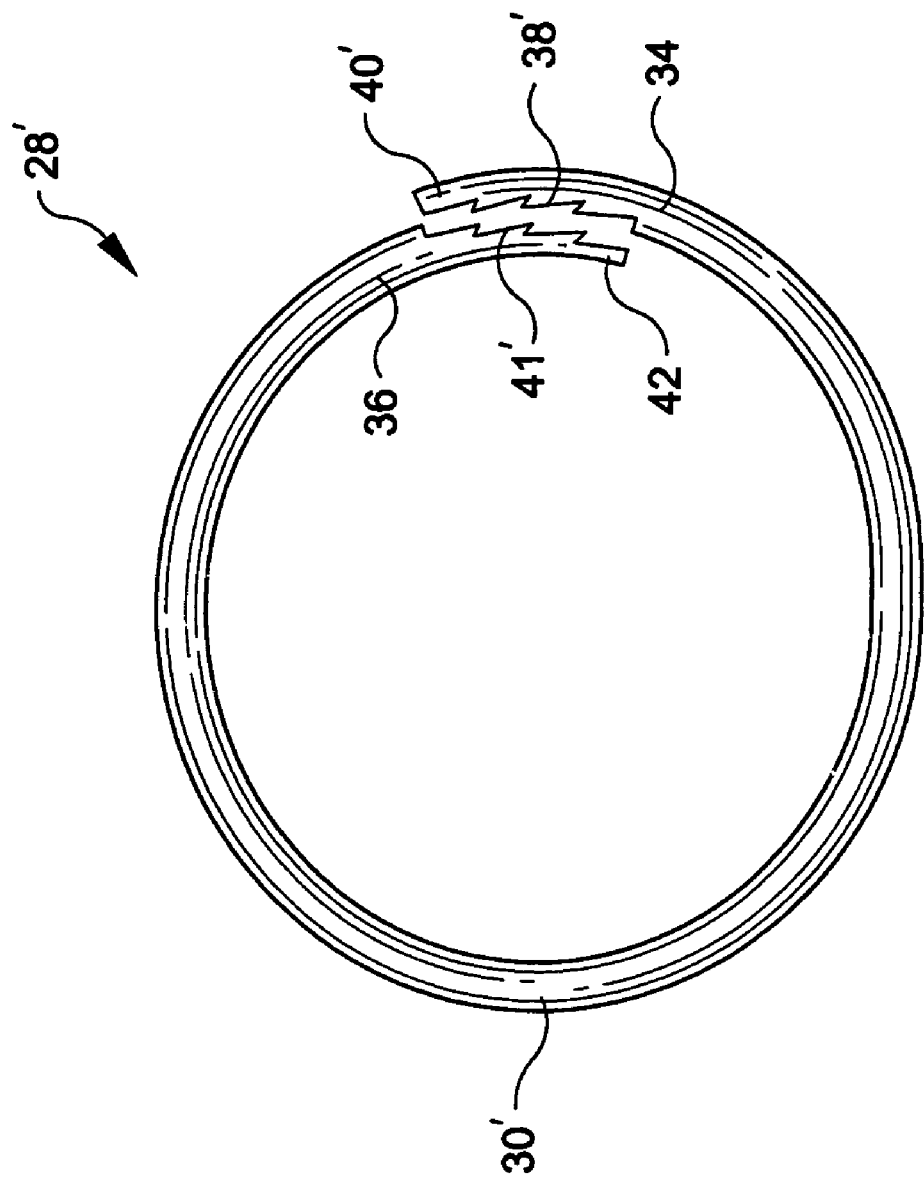
FIG. 3 is a front view of another embodiment of a stent of the composite graft-stent of FIG. 1.

Now with reference to FIG. 3, a further embodiment of the stent of the present invention is shown. Stent 28' may be formed from a wire employing a simple "ratchet" design. The wire 30' is formed in a circular configuration and includes a first end 34' adjacent to and overlapping its second opposed end 36'. Several ratchet-like teeth 38' are located at an end extent 40' of the first end 34'. The other end 36' includes a pawl 41' at a distal end 42' thereof for adjustable engagement with teeth 38'. Upon relative movement of opposed ends 34' and 36', teeth 38' are engaged by pawl 41' to provide adjustable interlocking therebetween. This allows the diameter of the circular stent 28' to be adjustably expanded in incremental fashion, to set the diameter thereof at discrete increments.

Figure 4:
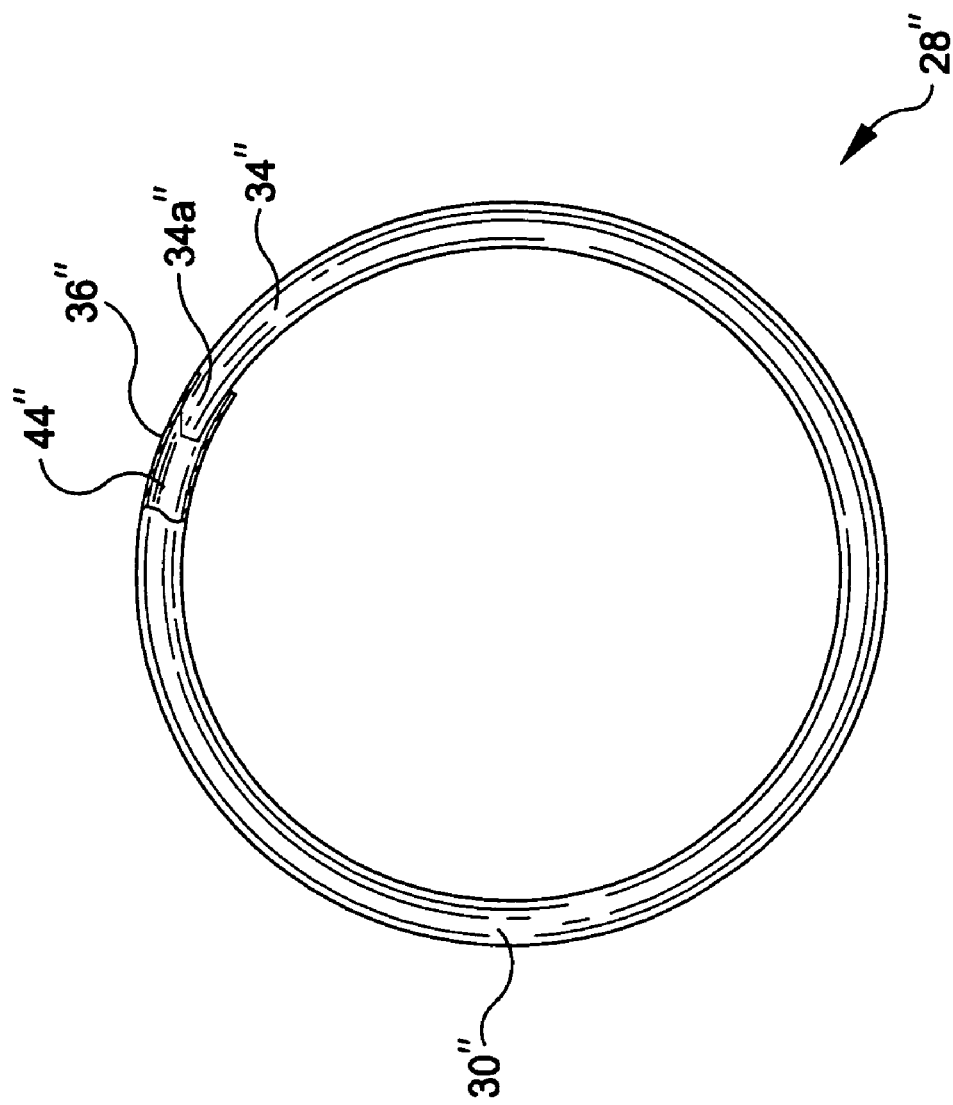
FIG. 4 is a front view, partially in section of a still further embodiment of a stent of the composite graft-stent of FIG. 1.

Now with reference to FIG. 4, an additional embodiment of a stent is shown. Stent 28" is a wire stent employing telescoping-ends. The wire 30" is formed in a circular configuration and includes a first end 34" that is positioned in general axial alignment with a second opposed end 36". A distal portion 34a" of first end 34" telescopes into an elongate open-ended channel 44" formed at opposed end 36". The diameter of the stent 28" is contracted and expanded by movement of first end 34" into and out of open-ended channel 44".

The various embodiments of each of the stents 28 described herein are preferably manufactured out of a bio-compatible metal. Most preferably, the bio-compatible metal is stainless steel, platinum, gold, nitinol, tantalum and alloys thereof.

One or more such stents 28 may be disposed between tubes 12 and 22. For example, in one embodiment a single stent 28 is disposed about one end of tube 12. In an alternative embodiment of the invention, two stents 28 are disposed about each end of tube 12. In yet another embodiment of the invention, several stents 28 are disposed about the exterior surface 18 of tube 12 and are longitudinally spaced therealong between the two ends 14 and 16 of tube 12.

While the preferred embodiments of the invention are shown and described below, other embodiments that fall within the scope of the disclosure and appended claims are also contemplated.

The invention being thus described, it will be obvious that the same may be varied in many ways. Such variations are not to be regarded as a departure from the spirit and scope of the invention and all such modifications are intended to be included within the scope of the following claims.

What is claimed is:

1. An implantable stent-graft device comprising:
   a first elongate tubular graft structure;
   a second elongate tubular graft structure disposed concentrically over and secured to said first tubular graft structure; and
   a plurality of radially expandable ring stent members disposed at spaced apart locations between said first and second tubular graft structures, each said stent member including a first end and an opposed second end adjacent and overlapping said first end, said first end including a plurality of ratchet teeth and said second end including a pawl for engagement with said teeth of said first end for adjustable interlocking engagement therewith said stent members being secured between said first and second tubular graft structures so as to permit radial expansion of said device and said stent members being relatively longitudinally immobilized by said securement of said first tubular graft structure to said second tubular graft structure.

2. An implantable stent-graft device of claim 1, wherein said stent is made of a bio-compatible metal.

3. An implantable stent-graft device of claim 2, wherein said bio-compatible metal is selected from the group consisting of stainless steel, platinum, gold, nitinol, tantalum and alloys thereof.

4. An implantable stent-graft device of claim 1, wherein said first and second tubular graft structures are made from expanded polytetrafluoroethylene.

* * * * *